US006929735B2

(12) United States Patent
Prohaska et al.

(10) Patent No.: US 6,929,735 B2
(45) Date of Patent: Aug. 16, 2005

(54) ELECTROCHEMICAL SENSOR HAVING IMPROVED RESPONSE TIME

(75) Inventors: Otto J. Prohaska, Seymour, CT (US); Avinash Dalmia, Hamden, CT (US)

(73) Assignee: Perkin Elmer Instruments LLC, Shelton, CT (US)

( * ) Notice: Subject to any disclaimer, the term of this patent is extended or adjusted under 35 U.S.C. 154(b) by 0 days.

(21) Appl. No.: 10/345,772

(22) Filed: Jan. 16, 2003

(65) Prior Publication Data

US 2003/0106811 A1 Jun. 12, 2003

Related U.S. Application Data

(63) Continuation-in-part of application No. 09/443,875, filed on Nov. 19, 1999, now Pat. No. 6,682,638.

(51) Int. Cl.⁷ ............................................. G01N 27/407
(52) U.S. Cl. ..................... 205/783.5; 204/424; 204/426
(58) Field of Search ................. 204/421–429; 205/783.5

(56) References Cited

U.S. PATENT DOCUMENTS

| | | |
|---|---|---|
| 3,934,193 A | 1/1976 | Hall |
| 3,972,682 A | 8/1976 | Stephens et al. |
| 4,032,296 A | 6/1977 | Hall |
| 4,038,053 A | 7/1977 | Golay |
| 4,172,770 A | 10/1979 | Semersky et al. |
| 4,440,726 A | 4/1984 | Coulson |
| 4,555,383 A | 11/1985 | Hall |
| 4,032,296 A | 1/1987 | Hall |
| 4,649,124 A | 3/1987 | Hall |
| 4,812,221 A * | 3/1989 | Madou et al. |
| 4,820,386 A | 4/1989 | LaConti et al. |
| 4,851,104 A | 7/1989 | Connery et al. |
| 4,900,405 A * | 2/1990 | Otagawa et al. |
| 5,194,814 A | 3/1993 | D'Couto |
| 5,302,274 A | 4/1994 | Tomantschger et al. |
| 5,331,310 A | 7/1994 | Stetter et al. |
| 5,525,197 A | 6/1996 | Coulson |
| 5,527,446 A * | 6/1996 | Kosek et al. |

(Continued)

FOREIGN PATENT DOCUMENTS

| | | |
|---|---|---|
| DE | 199 40 095 A1 | 1/2001 |
| DE | 199 44 650 A1 | 12/2001 |
| EP | 0 157160 A1 | 9/1985 |
| GB | 1382640 | 6/1972 |
| GB | 1382649 | 8/1972 |

OTHER PUBLICATIONS (Polyaniline thin–films for gas sensing), N.E. Agbor et al., 1995 Elsevier Science S.A. pp. 173–179.

(Continued)

*Primary Examiner*—Kaj K. Olsen
(74) *Attorney, Agent, or Firm*—St. Onge Steward Johnston & Reens LLC

(57) ABSTRACT

The invention relates to a method and apparatus for providing an electrochemical gas sensor having improved response time for detecting a gas introduced into the sensor. The sensor includes a substrate having a first surface and a second surface and an electrode deposited on the first surface. The sensor also includes an ionomer membrane in contact with the first surface and the electrode. The ionomer membrane has an opening in a location proximate to the electrode for permitting gas introduced into the sensor to diffuse through the opening to simultaneously contact the electrode and the ionomer membrane within the opening. The substrate further includes at least one hole extending from the first surface to the second surface for permitting moisture to diffuse through the at least one hole to contact the ionomer membrane for enhancing sensitivity.

19 Claims, 3 Drawing Sheets

U.S. PATENT DOCUMENTS

| | | | |
|---|---|---|---|
| 5,545,252 A | | 8/1996 | Hinshaw et al. |
| 5,573,648 A | | 11/1996 | Shen et al. |
| 5,650,054 A | * | 7/1997 | Shen et al. |
| 5,711,786 A | | 1/1998 | Hinshaw |
| 5,830,337 A | * | 11/1998 | Xu |
| 5,889,197 A | | 3/1999 | Van der Maas et al. |
| 5,985,673 A | | 11/1999 | Bao et al. |
| 6,080,294 A | * | 6/2000 | Shen et al. |
| 6,165,251 A | | 12/2000 | Lemieux et al. |
| 6,200,443 B1 | | 3/2001 | Shen et al. |
| 6,205,841 B1 | | 3/2001 | Shibamoto |
| 6,245,298 B1 | | 6/2001 | Bremer et al. |
| 6,287,643 B1 | | 9/2001 | Powell et al. |
| 6,306,489 B1 | | 10/2001 | Hellmann et al. |
| 6,309,612 B1 | | 10/2001 | Balachandran et al. |
| 6,338,823 B1 | | 1/2002 | Furukawa |
| 6,355,150 B1 | | 3/2002 | Savin-Poncet et al. |
| 6,682,638 B1 | * | 1/2004 | Prohaska et al. ........... 204/426 |

OTHER PUBLICATIONS (The Development of a Thick–Film Electrochemical Sensor and Instrumentation for In–Situ Determination of Carbon Dioxide Partial Pressure ($pCO_2$) In The Marine Environment), M.R. Creasey et al., University of Southampton, U.K., Electronic Engineering in Oceanography, Jul. 19–21 1994, Conference Publication No 394 IEE 1994.

(Sixth International Conference on Electronic Engineering in Oceanography) Electron theory of thin–film gas sensors, Helmut Geistlinger, 1993 Elsevier Sequoia, pp 47–60.

(A Practical Reference Electrode) J. Giner, Pratt & Whitney Aircraft, Division of United Aircraft Corporation, East Hartford, CT.

(Design and application of thick–film multisensors) N. Hampp et al., 1992 Elsevier Sequoia pp. 144–148.

(Thin Film Porous Membranes for Catalytic Sensors) R.C. Hughes, et al., 1997 International Conference on Solid–State Sensors and Actuators Chicago, Jun. 16–19, 1997.

(Amperometric Gas Sensor of Thin Gold Film Electrode Ion–Plated on Gas Permeable Membrane for Detection of Arsine and Silane) Toru Ishiji et al., pp. 1019–1020.

(A solid–state pH sensor based on a Nafion–coated iridium oxide indicator electrode and a polymer–based silver chloride reference electrode) Patrick J. Kinlen et al., 1994 Elsevier Science pp 13–25.

(Multifunctional Sensors Based on Ceramic Electrolytes) Meilin Liu et al., Georgia Institute of Technology, Atlanta, Georgia pp 421–427.

(The thick–film route to selective gas sensors) F. Menil et al., 1995 Elsevier Science S.A. pp 415–420.

(Properties of vanadium oxide thin films for ethanol sensor) G. Micocci et al., J. Vac. Sci. Technol. A 15(1), Jan./Feb. 1997 American Vacuum Society.

(An Integrated Multi–Element Ultra–Thin–Film Gas Analyzer) N. Najuh et al., Solid–State Sensor and Actuator Workshop Proc. 5.

(Preparation of thin gold–film electrode for an electrochemical gas sensor for phosphine and arsine) Nobuo Nakano, et al., 1994 Elsevier Science S.A. pp 51–55.

(A Study of the Surface Sensitivity of Tin Oxide Sensors to Carbon Monoxide and Dioxide) Dario Narducci et al., Dept. of Physical Chemistry & Electrochemistry v. C. Golgi, 19 I–20133 Milano (Italy).

(UV–Polymerizable Screen–Printed Enzyme Pastes) Ingrid Rohm, et al., 1995 American Chemical Society Analytical Chemistry, vol. 67, No. 13, Jul. 1, 1995, Anal. Chem. 1995, 67 2304–3207.

(CO–Sensor for domestic use based on high temperature stable $Ga_2O_3$ thin films), T. Schwebel, et al., 1997 International Conference on Solid–State Sensors and Actuators Chicago, Jun. 16–19, 1997.

(A Low–Power CMOS Compatible Integrated Gas Sensor Using Maskless Tin Oxide Sputtering) Lie–yi Sheng, et al., 1997 International Conference on Solid–State Sensors and Actuators Chicago, Jun. 16–19, 1997 pp 939–942.

(Platinum Thin Films and Next–Generation Micromachined Sensors) John Staley, et al., Sensors Apr. 1996.

(An amperometric carbon monoxide sensor based on the steady–state difference response technique) Y. Tan et al., 1995 Elsevier Science S.A. pp 113–121.

(A Novel Semiconductor No Gas Sensor Operating At Room Temperature) Zhang Wenyi et al., 1997 International Conference on Solid–State Sensors and Actuators, Chicago, Jun. 16–19, 1997.

(Environmental gas sensing) Noboru Yamazoe et al., 1994 Elsevier Science S.A. pp 95–102.

(Life–elongation mechanism of the polymer–electrolyte lamination on a CO sensor) Ayumu Yasuda, et al., 1994 Elsevier Science S.A. pp 229–236.

Analytik Jena AG acquires 100% of APS Technologies, Inc./USA Jena/Houston, Sep. 24, 2001, 2 pgs.

Total Sulfur Analyzer—Combustion / Electrochemical Detection*; APS Technologies, Inc.; ASTM D6428–99; 40 CFR 80.580; 2 pgs.

Versatile Electrolytic Conductivity Detector For Gas Chromatography, P. Jones and G. Nickless, J. Chromatogr., 73 (1972), 19–28.

Electrolytic Conductivity Detector for Gas Chromatography, Dale M. Coulson, Coulson Instruments Co., J. Gas Chromatography, Apr. 1965.

Carbon Monoxide Sensors, Beech et al., Electrochemistry at Loughborough, 1999.

* cited by examiner

ELECTROCHEMICAL SENSOR HAVING IMPROVED RESPONSE TIME

PRIORITY APPLICATION

This application is a Continuation-in-Part application of U.S. patent application Ser. No. 09/443,875 for a "Film Type Solid Polymer Ionomer Sensor and Sensor Cell" filed Nov. 19, 1999 now U.S. Pat. No. 6,682,638 B1.

FIELD OF THE INVENTION

The invention relates to an electrochemical gas sensor having an improved response time.

BACKGROUND OF THE INVENTION

Detecting gases is useful for a variety of reasons. With respect to environmental concerns, an apparatus for detecting pollution or industrial emission is beneficial to help limit such contaminants entering water systems or the atmosphere. A gas detection unit may also be used for detecting the presence of dangerous chemical compounds, such as carbon monoxide, in a mixture of gases. In the medical field, a gas detection unit may be used for detecting a particular gas in equipment, such as an oxygen inhalation machine, for alerting staff as to the amount of oxygen remaining in the reservoir or given to the patient.

Known methods and apparatuses have been developed to detect the presence of gases. Typical systems include gas chromatography, ion chromatography, electrolytic conductivity detection, and conductometric measurement. However, these manners for detecting gases have generally been expensive, cumbersome, or shown to have low sensitivities and slower response times. In situations where a generally quick response time may be desired, such as detecting toxic gases or a lack of oxygen in an oxygen inhalation machine, gas detection systems having enhanced abilities to quickly detect particular gases are usually favorable.

Electrochemical sensors were provided to overcome these limitations. Electrochemical sensors typically provide signals which tend to exhibit acceptable sensitivity and usually have quick response times relative to gas chromatography, ion chromatograph, and electrolytic conductivity detection systems.

Other electrochemical gas sensors typically include metal layers or electrodes in contact with and beneath an electrolytic film of, for example, Nafion or Teflon. However, because the gas usually needs to diffuse through the ionic medium before reaching the sensing electrode, the response time may be negatively affected.

Recently, planar thin film sensors have been developed by constructing three planar electrodes on an insulating substrate and covering them with a thin polymer electrolyte, such as Nafion. J. A. Cox and K. S. Alber, *Amperometric Gas Phase Sensor for the Determination of Ammonia in a Solid State Cell Prepared by a Sol-Gel Process*, 143, No. 7 J. Electrochem. Soc. L126–L128 (1996) developed a solid state cell in which microelectrode arrays were coated with a film of vanadium oxide xerogel for detection of ammonia. However, this film needs to be soaked in an electrolyte solution in order to provide ionic conductivity. These methodologies, in which a planar substrate with metal electrodes is covered with a thin film of solid state electrolytic material, are suitable for automated mass production, but they have longer response times since gas needs to diffuse through a relatively thick film of electrolyte.

As shown electrochemical gas sensor 10 includes substrate 11, electrode 3, and ionomer membrane 5. Gas enters and exits sensor 10 through the inlet and outlet as shown. A portion of the gas entering sensor 10 diffuses through diffusion hole 20 and contacts electrode 3, which detects the type of gas present in sensor 10.

To enhance sensitivity to sensor 10, a reservoir 9 is provided containing electrolyte solution to wet ionomer membrane 5. As shown, reservoir 9 and, therefore, the electrolyte solution is in contact with ionomer membrane 5. Because reservoir 9 is located on a same side of ionomer membrane 5 as diffusion hole 20, a length of diffusion hole is typically at least as long as a height of reservoir 9.

What is desired, therefore, is an electrochemical sensor that overcomes the limitations of the prior art to provide a further improved response time. What is also desired is an electrochemical sensor having a wetted electrolytic medium to maintain sensitivity. A further desire is to provide an electrochemical sensor having a diffusion control passage for controlling the flow of gas leading to the sensing electrode.

SUMMARY OF THE INVENTION

Accordingly, it is an object of the invention to provide an electrochemical gas sensor having an improved response time.

It is an object of the invention to provide an electrochemical gas sensor having improved sensitivity.

A further object of the invention to provide an electrochemical gas sensor having a control passage for controlling the flow of gas leading to the sensing electrode and/or for controlling the flow of electrolyte solution to wet the ionomer membrane.

These and other objects of the invention are achieved by provision an electrochemical gas sensor for detecting a gas having a substrate having a first surface and a second surface and an electrode deposited on the first surface. The sensor also includes an ionomer membrane in contact with the first surface and the electrode. The ionomer membrane has an opening in a location proximate to the electrode for permitting gas introduced into the sensor to diffuse through the opening to simultaneously contact the electrode and the ionomer membrane within the opening. The substrate further includes at least one hole extending from the first surface to the second surface for permitting moisture to diffuse through the at least one hole to contact the ionomer membrane for enhancing sensitivity.

The invention further includes a reservoir for containing moisture, or electrolyte solution, to moisten the ionomer membrane. In some embodiments, the reservoir may be located adjacent to the substrate on a side of the substrate opposite the ionomer membrane. The electrolyte solution diffuses from the reservoir through the at least one hole in the substrate to contact the ionomer membrane on the opposite side of the substrate.

The sensor may optionally include a wicking material in contact with the second surface to facilitate drawing moisture from the reservoir toward the substrate. In some embodiments, the wicking material may be located in the at least one hole of the substrate.

In other embodiments, the reservoir may be spaced apart from the second surface and the wicking material may be between the second surface and the reservoir. Optionally, the substrate may also be a thin foil. The sensor may further include a film of electrolytic material on the electrode to increase a three phase contact between the gas, electrode, and ionomer membrane.

In another aspect, the invention includes a method for detecting a gas, including the steps of providing a substrate having a surface, providing at least one hole in the substrate that extends from a first surface of the substrate to a second surface of the substrate, and depositing an electrode on the first surface. The method further includes the steps of contacting an ionomer membrane with the electrode, providing an opening in the ionomer membrane in an approximate area of the electrode, introducing a gas into the opening toward the electrode, and simultaneously contacting the gas with both the electrode and ionomer membrane.

The method may further include the step of providing a reservoir containing moisture to moisten the ionomer membrane, wherein the the reservoir is positioned adjacent to the substrate on a side of the substrate opposite the ionomer membrane.

The method includes the step of diffusing moisture from the reservoir to the at least one hole to contact the ionomer membrane.

Optionally, the method includes the step of placing a wicking material in contact with the second surface and a solution in the reservoir for drawing moisture from the reservoir toward the substrate. In some embodiments, the method may include placing a wicking material in the at least one hole.

The method may also include the step of directing gas through the opening toward the electrode. Additionally, the method may further include the step of controlling the gas as it passes through the opening toward the electrode. Similarly, the method may include the step of controlling the solution as it passes through the at least one hole in the substrate.

To enhance detection of the gas being introduced into the sensor, the method may include the steps of oxidizing the gas as the gas contacts the surface of the electrode and/or reducing the gas as the gas contacts the surface of the electrode.

The invention and its particular features and advantages will become more apparent from the following detailed description considered with reference to the accompanying drawings.

DETAILED DESCRIPTION OF THE DRAWINGS

Figure 1:
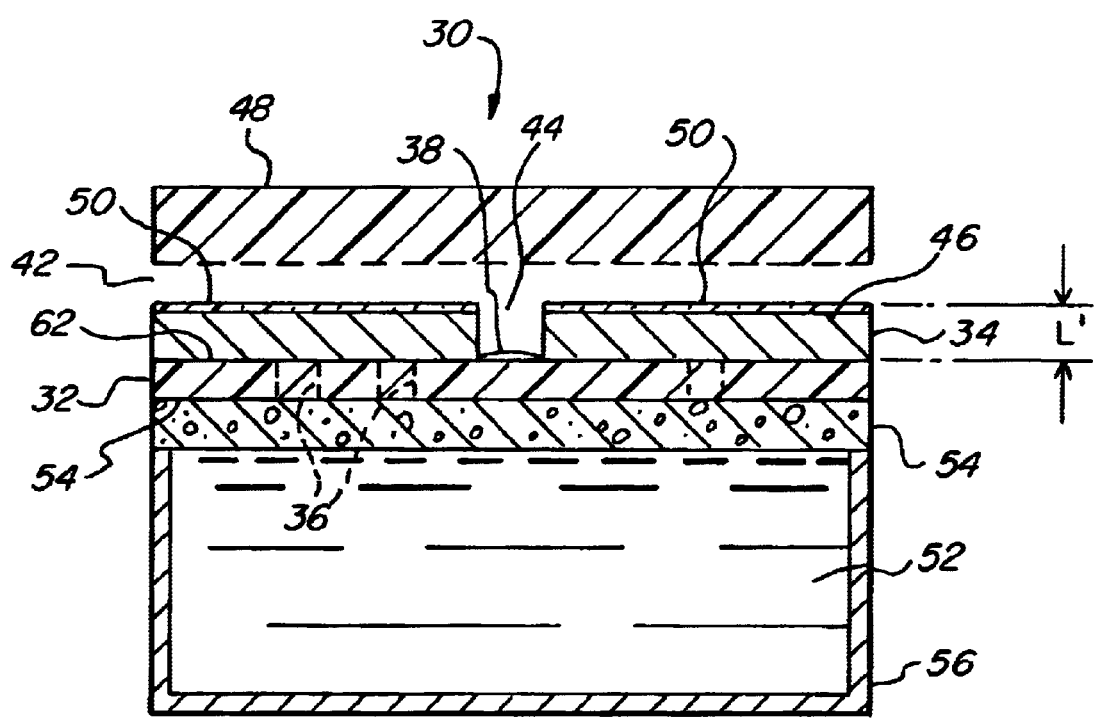
FIG. 1 depicts an electrochemical gas sensor in accordance with the invention.

FIG. 1 depicts the electrochemical gas sensor 30 in accordance with the invention. Sensor 30 includes substrate 32, ionomer membrane 34, and electrode 38 placed within housing 48. Gas enters sensor 30 through inlet 42 and is detected after diffusing through diffusion hole 44 to contact electrode 38, which is in contact with ionomer membrane 34. Gas exits sensor 30 through outlet 46. It is understood that the gas may flow in a reversed direction where outlet 46 is the inlet and inlet 42 is the outlet.

Sensor 30 of FIG. 1 overcomes this disadvantage by wetting ionomer membrane 34, via hole 36 in substrate 32, with solution 52 located on a side of substrate 32 opposite from electrode 38. Because of the position of reservoir 56, length L' can be shortened, thereby reducing gas diffusion time and improving the sensitivity of sensor 30. The more length L' is reduced, the faster the response time of sensor 30. In some embodiments, length L' is less than 1.4 mm. In other embodiments, length L' is less than 0.1 mm. In further, embodiments, length L' is less than 0.5 mm. In still further embodiments, length L' is less than 0.1 mm. In fact, length L' or a thickness of ionomer membrane 34 may be reduced until it is flush with or below a surface of electrode 38. In some embodiments, diffusion hole 44 is eliminated because length L' is flush with or below a surface of electrode 38. All that is required is for ionomer membrane 34, of any length L', to be in contact with electrode 38 so that gas entering through inlet 42 provide a desired gas/ionomer membrane/electrode interface.

As a result of the reduced length L' of sensor 30, the response time of sensor 30 is less than approximately 2 seconds, more preferably less than approximately 1 second, and most preferably less than approximately 0.5 seconds. In some embodiments, the response time is less than approximately 0.1 seconds.

To further enhance sensitivity, a thickness of substrate 32 is reduced to improve wetting by solution 52. Substrate 32 is of an electrically non-conductive material for providing a surface upon which electrode 38 is placed. Optionally, substrate 32 is a thin foil having insulative, or electrically non-conductive, properties, such as Kapton or any other material. The foil is not metallic or conductive. The foil may also be flexible as compared to ceramic or glass. The thickness of the foil, or substrate 32, is generally less than approximately 4 mils and preferably less than approximately 1 mil. The thinner substrate 32, the faster ionomer membrane 34 is wetted and this positively affects sensor response time. Therefore, as the thickness of substrate 32 approaches 0 mils, the response time is further reduced.

Optionally, in some embodiments, sensor 30 may include wicking material 54 to facilitate or enhance wetting of ionomer membrane 34 by solution 52. Wicking material 54 is typically of a material that absorbs liquid, such as a sponge. Hence, as shown in FIG. 1, wicking material 54 will draw solution 52 upwardly from reservoir 56 toward ionomer membrane 34.

As shown, reservoir 56 and substrate 32 are separable from one another where wicking material 54 is placed between reservoir 56 and substrate 32. In other embodiments, wicking material is placed within reservoir 56 and reservoir comes in contact with substrate 32. In further embodiments, substrate 32 and reservoir 56 are made not separable from one another but are formed as one unit. Wicking material 54 may optionally be used with any of these embodiments of reservoir 56 and substrate 32.

As shown in FIG. 1, substrate 32 further includes at least one hole 36 extending from a first surface 62 of substrate 32 to a second surface 64 of substrate 32, thereby forming a thru-hole, for permitting solution 52 to pass, or diffuse, through at least one hole 36 to contact ionomer membrane 34. In the embodiments where substrate 32 is a foil, or a thin non-conductive material, wicking material 54 would be positioned in a closer relationship to ionomer membrane 34 than where substrate 32 is of a thick material. Where substrate 32 is a foil, solution 52 absorbed by wicking material 54 would more easily wet ionomer membrane 34. Optionally, wicking material 54 would be in contact, through at least one hole 36, with ionomer membrane 34. In some embodiments, wicking material 54, in addition to or instead of being between substrate 32 and solution 52, is placed within at least one hole 36.

To further facilitate wetting of ionomer membrane 34 by solution 52, or optional wicking material 54, a plurality of holes 36 are placed in substrate 32. It is understood that hole 36 is of any diameter, length, shape, or dimension. Also, the more holes 36 in substrate 32, in any location, the better ionomer membrane 34 is wetted. Hence, the hole 36 or plurality of holes 36 may act as a form of wetting control to ionomer membrane 34, as too much wetting or too little wetting negatively affects sensitivity. Moreover, hole 36 may be, in addition or instead of being round, a square shaped or polygonal shaped hole. Hole 36 may further be a slit or aperture of any kind. All that is required of hole 36 is that it provides a passage from first surface 62 to second surface 64 so that solution 52 diffuses through hole 36 to contact ionomer membrane 34.

Figure 3:
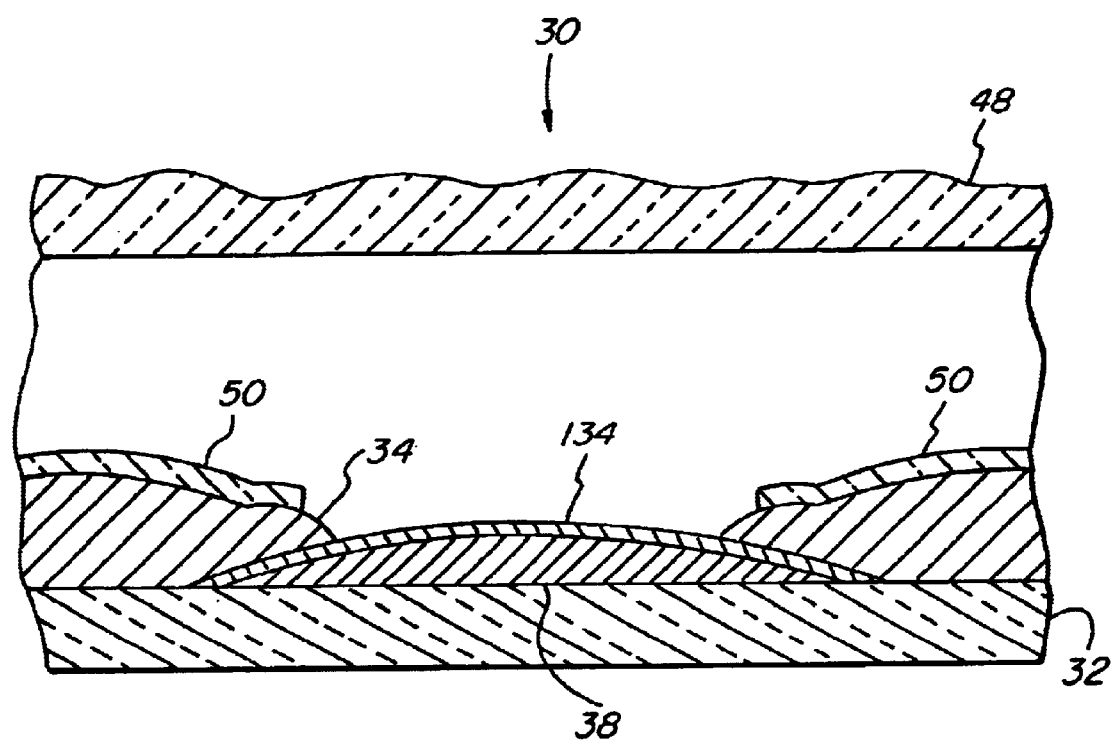
FIG. 3 depicts an exploded view of the electrode shown in FIG. 1.

As shown in FIG. 3, to enhance sensitivity of sensor 30 in some embodiments, a thin film 134 of ionomer membrane 34 may be placed on electrode 38 to increase the area of contact between ionomer membrane 34, electrode 38, and gas to include the surface of electrode 38. Gas diffuses throughout film 134, which is in contact with the surface of electrode 38. As a result of the increased contact area, the sensing area is increased and response time is minimized. Gas diffuses faster through film 134 when film 134 has a minimal thickness. Hence, the thinner film 134 is, the faster the response time is for sensor 30.

Without film 134, the interface in the approximate area of electrode 38 would be substantially smaller, limited to an area where ionomer membrane 34 comes in contact with electrode 38. This contact area would generally be a linear contact point defining an approximate circumference of electrode 38.

In some embodiments, film 134 has a thickness less than 2 micrometers. Ideally, film 134 should be as thin as possible to maximize sensor response time and sensitivity. Hence, sensor 30 may further comprise film 134 having a thickness of less than 1 micrometer. A film having such reduced thickness permits faster gas diffusion and, thus, faster response times. Film 134 is an electrolytic medium, which includes all the limitations of ionomer membrane 34 and may be, but need not be, the same material as ionomer membrane 34.

Film 134 is in a solid state or dry electrolyte for it has more structural integrity than liquid state electrolyte, thereby permitting a consistently uniform thickness over electrode 38. This enhances sensor repeatability and facilitates functionality for liquid state electrolyte would be difficult to maintain in a fixed position on the surface of sensing electrode 38.

Optionally, the response time of sensor 30 may further be improved by reducing the size of inlet 42 and outlet 46. In this effort, the gas is more concentrated while inside sensor 30 due to there being less internal volume for the gas to disperse. Less dispersion and a more concentrated gas generally results in a more easily detected gas and, therefore, reduced response time of sensor 30. As shown in FIG. 1, the dispersion in the horizontal direction is reduced, which is generally referred to as axial dispersion because the dispersion is approximately along the axis containing a center point of sensor 30, is reduced due to a reduction in size of inlet 42 and outlet 46. In some embodiments, inlet 42 and outlet 46 have a diameter of approximately 1 mm. Inlet 42 and outlet 46 need not be round but may be of any shape so long as gas may be injected into and extracted from sensor 30. Such shapes include 3 sided, 4 sided, or polygonal geometries.

Optionally, as shown in FIGS. 1 and 3, sensor 30 may also include cover 50 on ionomer membrane 34 for minimizing the vaporization or evaporation of solution 52 as solution 52 is absorbed and passed upwardly through ionomer membrane 34. Cover 50 is in contact with the surface of ionomer membrane 34 opposite from substrate 32. Cover 50 does not block any portion of either diffusion hole 44 or electrode 38 because doing so would hinder gas detection and negatively affect sensor sensitivity. Cover 50 is not needed for sensor 30 to operate properly and may be eliminated entirely from sensor 30. For embodiments where sensor 30 includes cover 50, it is understood that the length L' of the diffusion path is the height of both ionomer membrane 34 and cover 50. For embodiments where sensor 30 does not include cover 50, length L' is the height of membrane 34.

Figure 2:
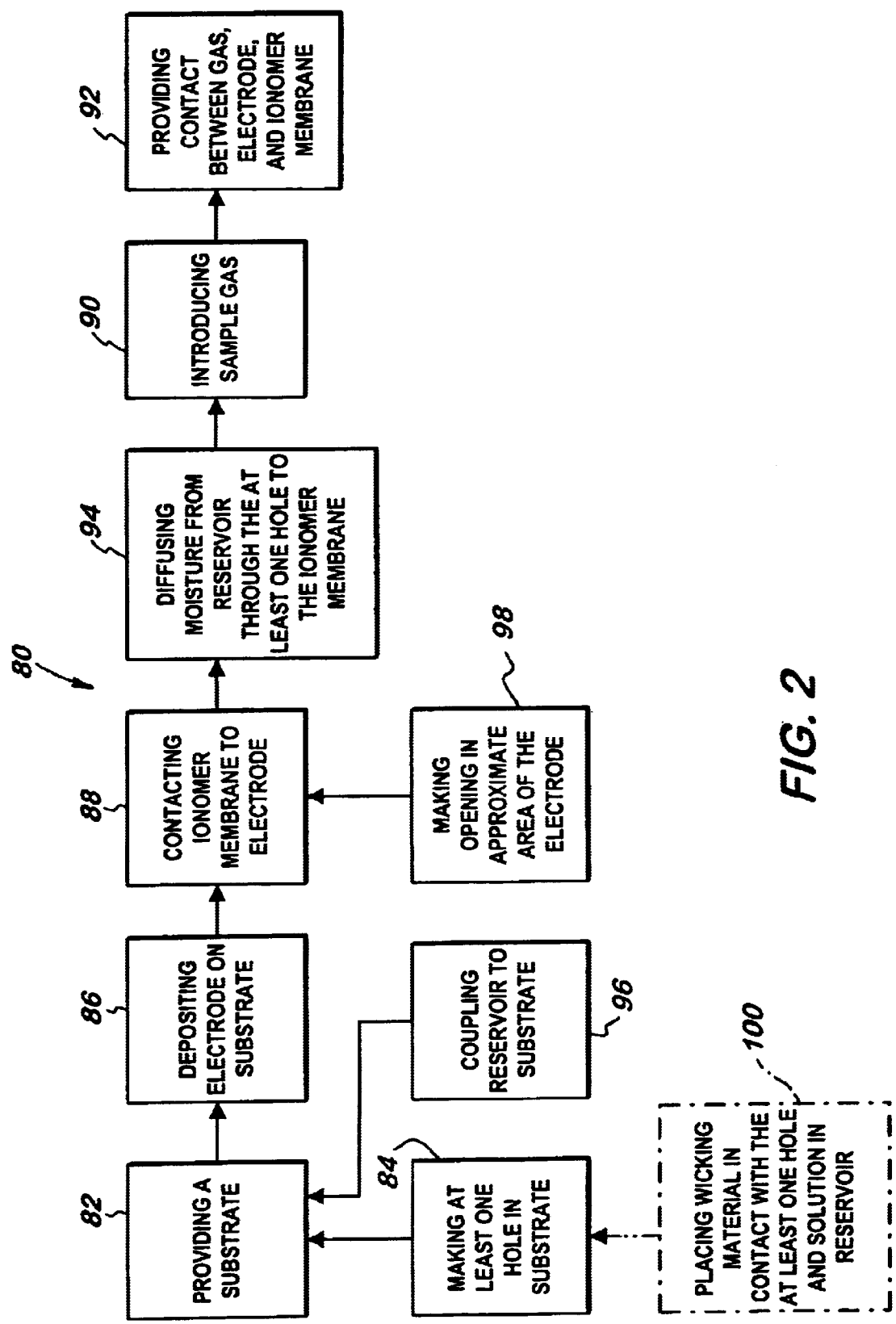
FIG. 2 depicts a method for providing the electrochemical gas sensor shown in FIG. 1.

In another aspect of the invention, a method 80 is shown in FIG. 2 for detecting a gas entering sensor 30 of FIG. 1. Method 80 includes the steps of providing 82 a substrate and providing 84 at least one hole in the substrate that extends from a first surface of the substrate to a second surface of the substrate. Method 80 also includes the steps of depositing 86 an electrode on the first surface, contacting 88 an ionomer membrane with the electrode, and providing 98 an opening in the ionomer membrane in an approximate area of the electrode. Method 80 further includes the steps of introducing 90 a gas into the opening toward the electrode and simultaneously contacting 92 the gas with both the electrode and the ionomer membrane. Detection includes oxidizing and/or reducing the gas.

Method 80 detects gas entering the sensor by directing some of the gas through the opening in the ionomer membrane and toward the electrode. By varying the diameter, length, or shape of the opening, method 80 controls the gas passing through the opening toward the electrode.

In some embodiments, method 80 may include providing 96 a reservoir containing moisture to wet the ionomer membrane so that the sensor's sensitivity is enhanced. In these embodiments, method 80 includes positioning the reservoir adjacent to the substrate and on a side of the substrate opposite the ionomer membrane. Solution for wetting the ionomer membrane is contained in the reservoir and comes in contact with the ionomer membrane by diffusing 94 through the at least one hole in the substrate.

Optionally, method 80 includes placing 100 wicking material, such as a sponge or other liquid absorbing material, in contact with the second surface of the substrate and the solution in the reservoir. In this position, the wicking material will draw the solution from the reservoir upwards toward the ionomer membrane. In some embodiments, method 80 includes placing wicking material in the at least one hole of the substrate to further facilitate wetting of the ionomer membrane.

Method may also control wetting, or the amount of solution passing through the at least one hole, the ionomer membrane by increasing or decreasing the amount of holes in the substrate and/or varying the diameter, length, or shape of the at least one hole in the substrate.

Although the invention has been described with reference to a particular arrangement of parts, features and the like, these are not intended to exhaust all possible arrangements or features, and indeed many other modifications and variations will be ascertainable to those of skill in the art

What is claimed is:

1. An electrochemical gas sensor for detecting a gas, comprising:
   a substrate having a first surface and a second surface;
   an ionomer membrane in contact with said first surface and having a proximal outermost surface and a distal outermost surface;
   an electrode in contact with said first surface;
   an opening in said ionomer membrane extending from said proximal outermost surface to said distal outermost surface in a location proximate to said electrode for defining a passage for gas to simultaneously contact said electrode and said ionomer membrane within said opening;
   said substrate further including at least one hole extending from said first surface to said second surface for permitting moisture to diffuse through said at least one hole to contact said ionomer membrane;
   a reservoir for containing moisture to moisten said ionomer membrane; and
   said reservoir is located on a side of said substrate opposite said ionomer membrane.

2. The electrochemical gas sensor according to claim 1, wherein said reservoir is located adjacent to said substrate.

3. The electrochemical gas sensor according to claim 1, wherein said opening extends from a first surface to a second surface of said ionomer membrane for defining walls to guide the gas to said sensing electrode.

4. The electrochemical gas sensor according to claim 1, said at least one hole further comprising moisture, said moisture being diffused from said reservoir to said ionomer membrane.

5. The electrochemical gas sensor according to claim 1, further comprising a wicking material in contact with said second surface for drawing moisture from said reservoir toward said substrate.

6. The electrochemical gas sensor according to claim 5, wherein said wicking material is located in said at least one hole of said substrate.

7. The electrochemical gas sensor according to claim 5, wherein said reservoir is spaced apart from said second surface and said wicking material is between said second surface and said reservoir.

8. The electrochemical gas sensor according to claim 1, further comprising a film of electrolytic material on said electrode to increase a three phase contact between the gas, said electrode, and said ionomer membrane.

9. The electrochemical gas sensor according to claim 1, wherein said substrate is a foil.

10. A method for detecting a gas, comprising the steps of:
    providing a substrate having a surface;
    providing at least one hole in the substrate that extends from a first surface of the substrate to a second surface of the substrate;
    depositing an electrode on the first surface;
    contacting an ionomer membrane with the electrode;
    providing an opening in the ionomer membrane extending from a proximal outermost surface to a distal outermost surface in an approximate area of the electrode;
    introducing a gas into the opening toward the electrode;
    simultaneously contacting the gas with both the electrode and ionomer membrane;
    providing a reservoir containing moisture to moisten the ionomer membrane; and
    positioning the reservoir on a side of the substrate opposite the ionomer membrane.

11. The method according to claim 10, further comprising the step of positioning the reservoir adjacent to the substrate.

12. The method according to claim 10, further comprising the step of diffusing moisture from the reservoir to the at least one hole.

13. The method according to claim 10, further comprising the step of placing a wicking material in contact with the second surface and a solution in the reservoir for drawing moisture from the reservoir toward the substrate.

14. The method according to claim 10, further comprising the step of placing a wicking material in the at least one hole.

15. The method according to claim 10, further comprising the step of directing gas through the opening toward the electrode.

16. The method according to claim 10, further comprising the step of controlling the gas as it passes through the opening toward the electrode.

17. The method according to claim 10, further comprising the step of controlling the solution as it passes through the at least one hole in the substrate.

18. The method according to claim 10, further comprising the step of oxidizing the gas as the gas contacts the surface of the electrode.

19. The method according to claim 10, further comprising the step of reducing the gas as the gas contacts the surface of the electrode.

* * * * *